United States Patent [19]
Iserin et al.

[11] Patent Number: 5,980,557
[45] Date of Patent: Nov. 9, 1999

[54] FASTENER FOR FASTENING A MUSCLE TENDON TO A BONE

[75] Inventors: Alain Iserin, Paris; Gilles Walsch, Lyons, both of France

[73] Assignee: Ethicon, Somerville, N.J.

[21] Appl. No.: 09/007,501

[22] Filed: Jan. 15, 1998

[51] Int. Cl.⁶ .................................................... A61B 17/04
[52] U.S. Cl. ......................... 606/220; 606/72; 606/213; 606/232
[58] Field of Search ............................... 606/72, 74, 213, 606/215, 216, 217, 232, 219, 220

[56] References Cited

U.S. PATENT DOCUMENTS

| | | | |
|---|---|---|---|
| 4,532,926 | 8/1985 | O'Holla | 606/220 |
| 5,478,353 | 12/1995 | Yoon | 606/213 |
| 5,520,691 | 5/1996 | Branch | 606/72 |

*Primary Examiner*—Michael Buiz
*Assistant Examiner*—David O. Reip
*Attorney, Agent, or Firm*—Emil Richard Skula

[57] ABSTRACT

A fastener for fastening a muscle tendon and muscle to a bone. The fastener has a shank designed to be inserted through a tendon and into a channel bored through a bone. A fastening head terminates the shank and is designed to come into abutment against the muscle and muscle tendon to hold the muscle and uscle tendon against the bone. A locking member is designed to cooperate with the shank at the distal end of the shank that emerges from a tunnel in bone in order to lock the shank end fastening head relative to the bone and to the muscletendon and muscle.

8 Claims, 3 Drawing Sheets

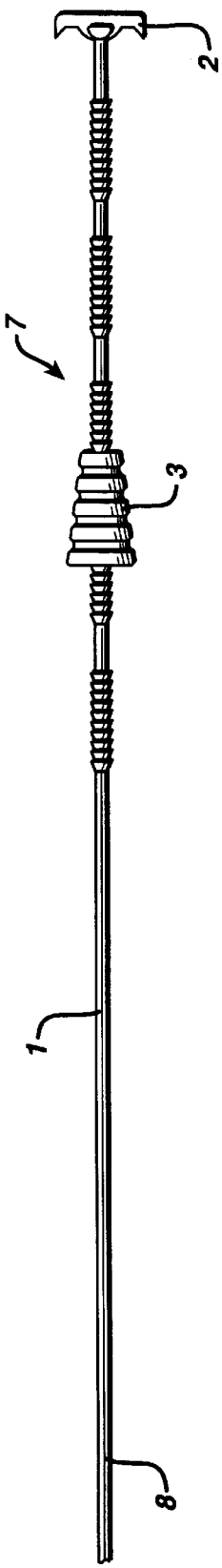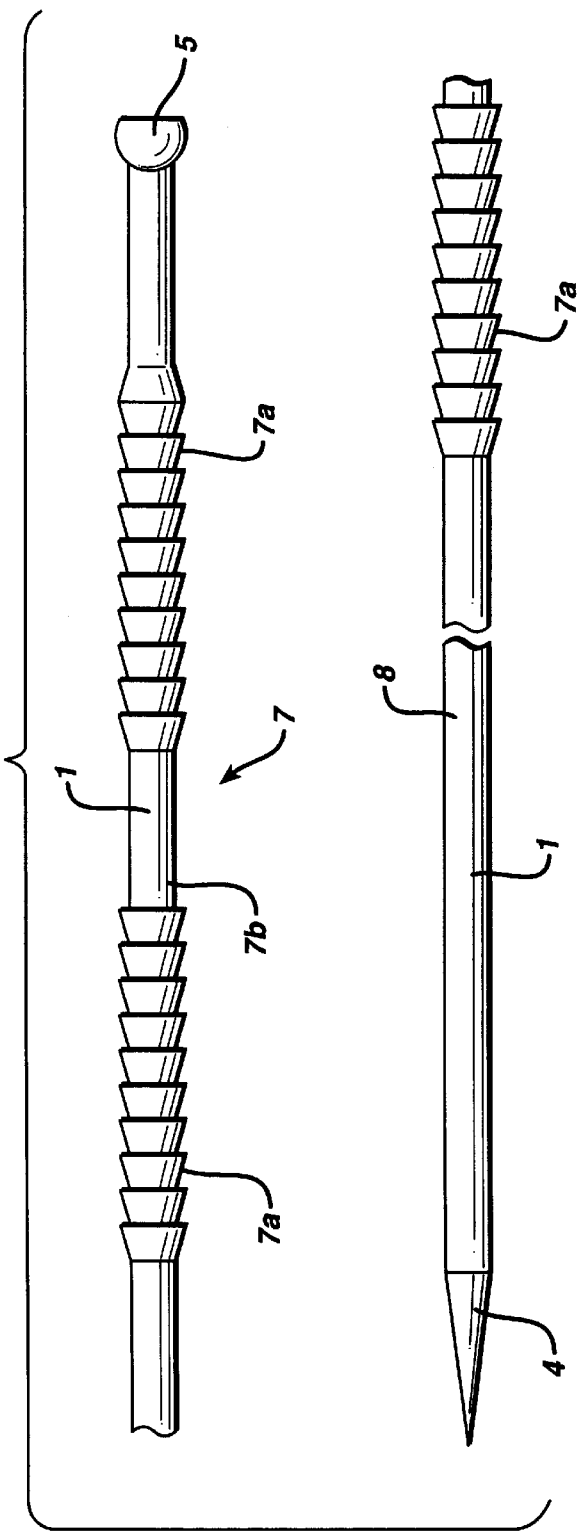

FASTENER FOR FASTENING A MUSCLE TENDON TO A BONE

FIELD OF THE INVENTION

The present invention relates to a fastener for fastening a muscle tendon to a bone.

A particularly advantageous application of the present invention is for fastening the muscles that are located on the top portion of the shoulder, referred to as "rotator cuff" muscles to the head of the humerus.

BACKGROUND OF THE INVENTION

Currently, muscles are fastened to bones by means of sutures.

It can be understood that such fastening is time-consuming and tedious to perform.

OBJECTS AND SUMMARY OF THE INVENTION

An object of the invention is to mitigate that drawback.

To this end, the invention provides a fastener for fastening a muscle tendon to a bone, said fastener comprising: a shank designed to be inserted through the tendon and through a channel bored through the bone; a fastening head which terminates said shank and which is designed to come into abutment against the muscle to hold it against the bone; and a locking member designed to co-operate with the shank at the end thereof that emerges from the tunnel through the bone to lock said shank and its head relative to the bone and to the muscle.

The fastener is advantageously supplemented by the various characteristics listed below, taken individually or in any of their technically possible combinations:

the shank is terminated by a ball on which the fastening head is swivel-mounted;

to co-operate with the locking element, the shank is provided with a plurality of serrations distributed uniformly over at least a portion of its length;

the shank is provided with a plurality of serrated zones disposed in alternation with smooth zones;

the locking element is a tube which is substantially frustoconical externally, and which is designed to be fastened to the bone by means of its frustoconical wall being clamped in the channel bored through the bone;

the locking element is provided with a plurality of internal serrations designed to co-operate with the serrations carried by the shank to enable the locking element to slide along the shank in one direction, and to prevent it from sliding therealong in the other direction;

the locking element is provided with annular recesses level with the internal serrations;

the head is provided with at least one spike for anchoring it in the muscle; and the head is provided with two lugs on respective sides of a central zone, each lug carrying an anchoring spike.

BRIEF DESCRIPTION OF THE DRAWINGS

Other characteristics and advantages of the invention appear from the following description given merely by way of non-limiting example and with reference to the accompanying drawings, in which:

FIG. 1 is a side view of a possible embodiment of a fastener of the invention;

FIG. 2 is a view in two portions showing the shank of the fastener shown in FIG. 1;

MORE DETAILED DESCRIPTION

Figure 3:
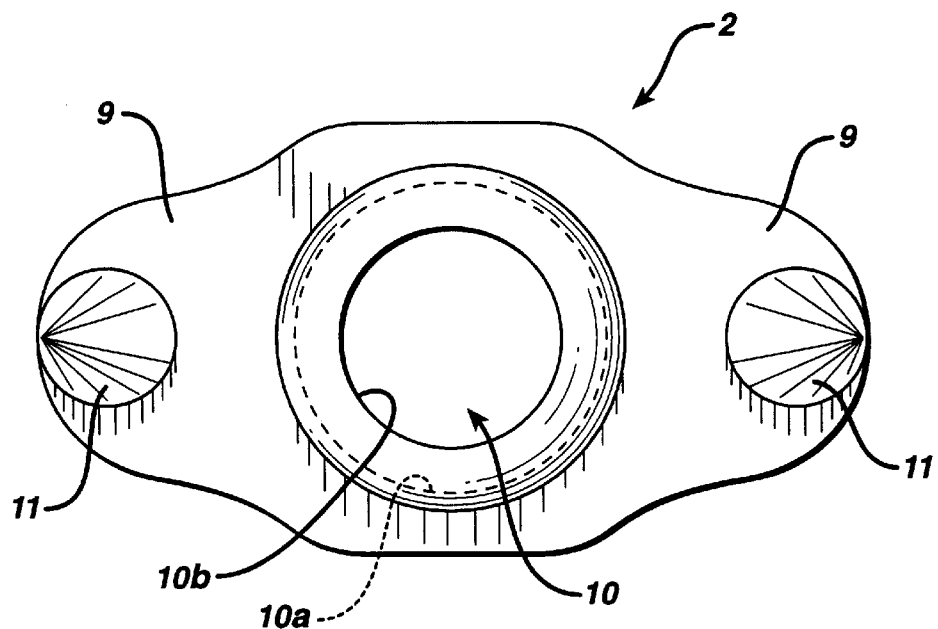
FIG. 3 is a view from above of the fastening head of the fastener shown in FIG. 1.

The fastener shown in FIG. 1 comprises a shank 1, a fastening head 2, and a locking element 3.

The shank 1, which is shown more specifically in FIG. 2, has a cylindrical body which is terminated at one end by a point 4 and at the other end by a hemispherical ball 5 (a sphere intersected by a flat that is perpendicular to the axis of the shank 1).

Over a portion of its length in the vicinity of the ball 5 (the portion being referenced 7 in the figures), the body of said shank 1 is provided with a plurality of serrated zones 7a distributed uniformly and separated by smooth zones 7b.

The serrated zones 7a are defined by successions of frustoconical teeth that flare towards the ball 5.

In the vicinity of the point 4, the shank 1 is terminated by a smooth portion 8.

Figure 4:
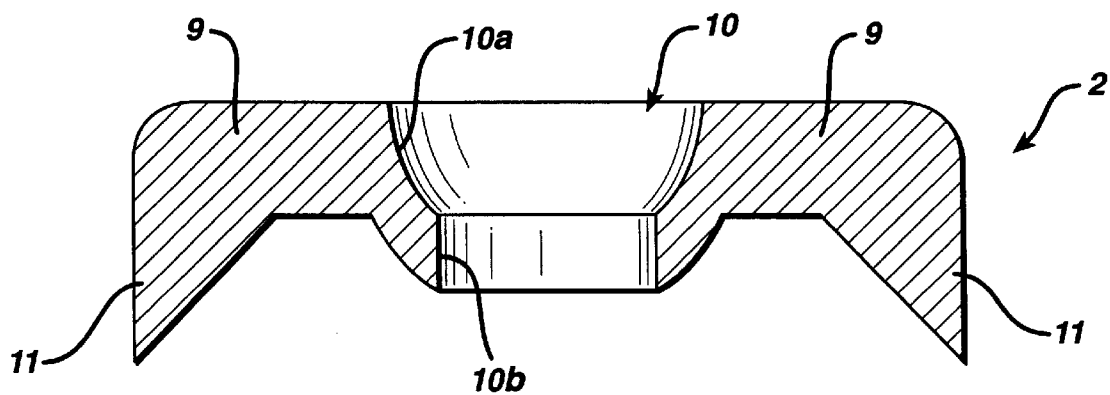
FIG. 4 is a section view of the fastening head shown in FIG. 3.

The fastening head 2 (FIGS. 3 and 4) has an elongate shape defined by two planar lugs 9 disposed on either side of a central zone 10.

The central zone 10 is provided with a through orifice which has a hemispherical portion 10a designed to co-operate with the ball 5 to enable the fastening head 2 to swivel relative to the shank 1. The central zone also includes a cylindrical portion 10b which extends from the bottom of the portion 10a.

The fastening head 2 is designed to be threaded onto the shank 1 via the point 4 thereof, and up the shank until the portion 10a caps the ball 5.

The inside diameter of the portion 10b is chosen to provide enough clearance relative to the diameter of the shank 1 and to the dimensions of the teeth of the serrated zones 7a for the head 2 to be threaded up along the shank 1, and for the angular position of said head 2 relative to said shank 1 to be adjusted.

Each of the planar lugs 9 carries a conical anchoring spike 11 on that one of its faces which is closer to the body of the shank 1 when the head 2 is in place on said shank 1.

Figure 5:
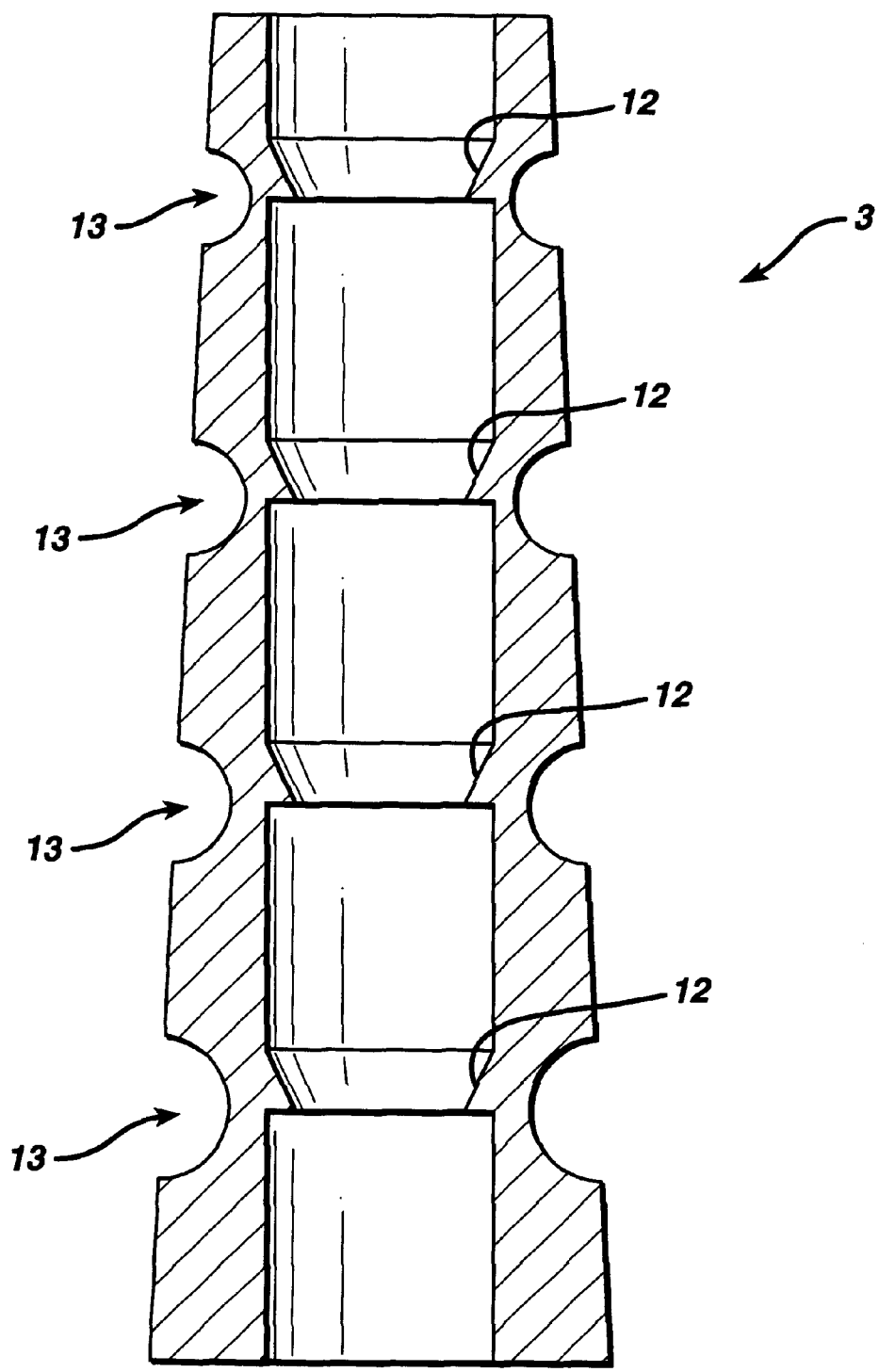
FIG. 5 is a section view of the locking element of the fastener shown in FIG. 1.

The locking element 3 (FIG. 5) is constituted by a tube that is substantially cylindrical internally and slightly frustoconical externally. Internally, the locking element 3 is provided with a plurality of serrations 12 serving to co-operate with the serrations on the shank 1.

The serrations 12 are constituted by resilient frustoconical catches which are designed to retract resiliently out of the way while the locking element is being slid up the shank 1 and to oppose any forces tending to cause said locking element 3 to slide back down along said shank 1.

The pitch of the serrations 12 is twice the pitch of the serrations on the zones 7a.

Semi-toroidal annular recesses 13 are provided on the external face of the locking element 3 level with the catches 12 to impart maximum resilience to said catches.

A possible example is given below for the dimensions of the shank 1, of the head 2, and of the locking element 3.

The diameter of the smooth portions of the shank 1 may be 1.5 mm.

The smooth portion 8 may be 95 mm long, the serrated portion 7 being 70 mm long.

Each serrated zone 7a of the portion 7 may be 10 mm high, with the smooth zones 7b disposed between said serrated zones each being 5 mm high.

The diameter of the large base of the teeth of the zone 7a is 2 mm.

For example, the ball 5 may have a diameter of 2.25 mm and a height of 1.5 mm.

The inside diameter of the orifice 10b through the head 2 is 1.6 mm.

The spikes 11 are 1 mm high, the lugs 9 being 0.8 mm thick.

The inside diameter of the element 3 is 2 mm, its height being 11 mm, its outside diameter varying from 4 mm to 2.9 mm.

For example, the frustoconical serrations 12 may be 0.5 mm high, the distance between the tips of two successive serrations 12 being 2.5 mm, for example.

In right section on planes containing the axis of the element 3, the annular recesses 13, of which there are four, are in the form of respective semi-circles whose radii lie in the range 0.6 mm to 0.4 mm.

The materials of the shank 1, of the head 2, and of the locking element 3 are resorbable (e.g. PLLA or PGA).

For example, the above-described fastener may be used as follows.

The surgeon prepares the bone to which the muscle is to be fastened by boring a tunnel through the bone, the inside diameter of the tunnel being, for example, 3.2 mm for fastener dimensions as given above.

With the fastening head 2 in place on the shank 1, said shank is inserted through the supraspinatus and then through the tunnel prepared by the surgeon through the bone.

The surgeon angularly positions the fastening head 2 as a function of the desired hold to be achieved on the muscle, and places said head so that it holds the muscle on the bone.

The locking element 3 is then threaded onto the shank 1 via the end thereof that emerges from the tunnel through the bone, and said locking element is slid up said shank 1 into the tunnel through the bone so that the frustoconical walls are clamped against the bone.

For example, the clamping pressure of the element 3 against the bone may be controlled by an instrument organized for this purpose.

The portion of the shank 1 that projects relative to the locking element is then cut off.

We claim:

1. A fastener for fastening a muscle tendon to a bone, said fastener comprising: a shank designed to be inserted through the tendon and through the channel bored through a bone, said shank having a proximal end and a distal end; a fastening head mounted to the proximal end of said shank such that the head is capable of swivel movement, said head having a hemispherical cavity wherein said shank is designed to come into abutment against the muscle to hold it against the bone; and a locking member designed to co-operate with the shank at the distal end thereof that emerges from the tunnel through the bone to lock said shank and its head relative to the bone and to the muscle, wherein the proximal end of the shank is terminated by a ball on which the fastening head is swivel-mounted by mating the ball with the hemispherical cavity of the fastening head.

2. A fastener according to claim 1, wherein, to co-operate with the locking member, the shank is provided with a plurality of serrations distributed uniformly over at least a portion of its length.

3. A fastener according to claim 2, wherein the shank is provided with a plurality of serrated zones disposed in alternation with smooth zones.

4. A fastener according to claim 1, where in the locking member is a tube which is substantially frustoconical externally, and which is designed to be fastened to the bone by means of its frustoconical wall being clamped in the channel bored through the bone.

5. A fastener according to claim 4, wherein to co-operate with the locking member, the shank is provided with a plurality of serrations distributed uniformly over at least a portion of its length, and wherein the locking member is provided with a plurality of internal serrations designed to co-operate with the serrations carried by the shank to enable the locking member to slide along the shank in one direction, and to prevent it from sliding therealong in the other direction.

6. A fastener according to claim 5, wherein the locking member is provided with annual recesses level with the internal serrations.

7. A fastener according to claim 1, wherein the head is provided with at least one spike for anchoring it in the muscle.

8. A fastener according to claim 7, wherein the head is provided with two lugs on respective sides of a central zone, each lug carrying an anchoring spike.

* * * * *

UNITED STATES PATENT AND TRADEMARK OFFICE
CERTIFICATE OF CORRECTION

PATENT NO. : 5,980,557
DATED : November 9, 1999
INVENTOR(S) : Alain Iserin, Gilles Walsch It is certified that error appears in the above-indentified patent and that said Letters Patent is hereby corrected as shown below:

On the Title page, Item [75] and [57] should read --

Inventors: WALSCH should be WALCH

ABSTRACT: Line 6 in Abstract, "uscle" should be "muscle"

--.

Signed and Sealed this

Sixteenth Day of May, 2000

Attest:

Q. TODD DICKINSON

*Attesting Officer*   *Director of Patents and Trademarks*